US00PP09165P

United States Patent [19]

van der Knaap

[11] Patent Number: Plant 9,165

[45] Date of Patent: Jun. 13, 1995

[54] CHRYSANTHEMUM PLANT NAMED 'RED CHAMPION'

[75] Inventor: Jacques C. M. van der Knaap, De Lier, Netherlands

[73] Assignee: Fides Beheer B.V., De Lier, Netherlands

[21] Appl. No.: 202,078

[22] Filed: Feb. 25, 1994

[51] Int. Cl.[6] ..... A01H 5/00

[52] U.S. Cl. ..... Plt./74.1

[58] Field of Search ..... Plt. 74.1, 82.4, 82.5

[56] References Cited

U.S. PATENT DOCUMENTS

P.P. 6,944 7/1989 Vanden Berg ..... Plt./82.5
P.P. 8,042 11/1992 van der Knaap ..... Plt./74.1
P.P. 8,641 3/1994 van der Knaap ..... Plt./74.1

*Primary Examiner*—Howard J. Locker

*Attorney, Agent, or Firm*—Burns, Doane, Swecker & Mathis

[57] ABSTRACT

A new and distinct cultivar of Chrysanthemum plant named Red Champion is provided. The new cultivar is a spontaneous mutation of the Champion cultivar (U.S. Ser. No. 08/202,201, filed concurrently herewith). The new cultivar forms attractive flat bi-toned reddish anemone flowers with a more intense coloration at the cushion. The plant exhibits a reduced susceptibility to leafminers, and the flowers exhibit a good vase life. The response period of the flowers is approximately seven to eight weeks. The new cultivar is particularly suited for use in the production throughout the year of a cut anemone spray or a pot mum under greenhouse conditions. An excellent tolerance to high temperatures is exhibited.

1 Drawing Sheet

SUMMARY OF THE INVENTION

The present invention comprises a new and distinct cultivar of Chrysanthemum, botanically known as *Chrysanthemum morifolium,* Ramat., and hereinafter is referred to by the cultivar name Red Champion. Alternatively, the botanical classification sometimes is expressed as *Dendranthema indicum.*

The new Red Champion cultivar is a spontaneous mutation of unknown causation which was discovered and carefully preserved during the course of plant selection work which was conducted by me. The new cultivar was discovered during April 1991 among plants of the Champion cultivar (U.S. Ser. No. 08/202,201, filed concurrently herewith) being grown under my direct supervision at De Lier, The Netherlands.

It was found that a single plant consistently formed flat bi-toned reddish anemone flowers (as illustrated) unlike the flat bi-toned pink anemone flowers of the Champion cultivar. All of the other characteristics of the new Red Champion cultivar were found to be substantially identical to those of the Champion cultivar. The distinctive mutant plant initially was designated 9104–822. Had I not discovered, carefully studied, and preserved this new cultivar, it would have been lost to mankind.

It was found that the new Chrysanthemum cultivar of the present invention:

(a) exhibits attractive flat bi-toned reddish anemone flowers wherein the disc florets are darker than the ray florets,
(b) exhibits a flower response period of approximately seven to eight weeks,
(c) forms flowers that exhibit a good vase life,
(d) exhibits a reduced susceptibility to leafminers, and
(e) has the ability to produce flowers of commercially acceptable quality throughout the year.

Cut flowers of the new cultivar commonly last approximately 14 days when placed in pure water following transport simulation for 2 days when present in a sleeve and boxed at room temperature. When present as a pot mum, the flowers commonly last approximately 3 weeks after the simulation of one week of darkness at 15° C.

The susceptibility to leafminers of the new cultivar is less than that of the standard resistant Penny Lane cultivar (U.S. Plant Pat. No. 6,238) and is more resistant than that of the standard susceptible Dark Pink Pompon cultivar (non-patented in the United States).

The new cultivar exhibits an excellent tolerance to high temperatures. Commonly Chrysanthemum plants are grown in greenhouses in The Netherlands while using nighttime temperatures of approximately 18° to 20° C., and daytime temperatures of approximately 18° C. with ventilation from 22° C. The Red Champion cultivar has been successfully grown during the summer in greenhouses wherein the temperature is approximately 6° C. higher during the daytime. Quality flowers can be produced throughout the year in a cut mum or a pot mum production program especially when grown in a 12 cm. pot. The flowers exhibit a good breaking ability.

Asexual reproduction of the new cultivar by vegetative cuttings are performed at De Lier, The Netherlands, in a controlled environment has demonstrated that the characteristics of the new cultivar as herein disclosed are firmly fixed and are retained through successive generations of asexual propagation.

Red Champion has not been observed under all possible environmental conditions to date. Accordingly, it is possible that the phenotype may vary somewhat with variations in the environment, such as temperature, light intensity, day length, contact with pesticides, and/or subjection to growth retardant treatments.

When the new cultivar of the present invention is compared to the Tasca cultivar (U.S. Plant Pat. No. 6,944), the Red Champion cultivar is found to exhibit a smaller flower size, a shorter response period, and a more intense coloration of the ray florets. The anemone type of flower, abundance of flowering, and excellent tolerance to high temperatures are similar to that exhibited by the Tasca cultivar.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown under greenhouse conditions at De Lier, The Netherlands.

DETAILED DESCRIPTION

The chart used in the identification of colors described hereinafter is the R.H.S. Colour Chart of The Royal Horticultural Society, London, England. The color values were determined between 11:00 a.m. and 12:00 noon under natural daylight conditions at De Lier, The Netherlands, during April of 1992. The plants described were grown under standard greenhouse conditions which approximate those commonly utilized for the production of cut mums.

Classification:

*Botanical.*—*Chrysanthemum morifolium* Ramat., cv. Red Champion.

*Commercial.*—Cut anemone spray, or pot mum.

Inflorescence:

A. *Capitulum.*—*Form.*—Flat.

*Type.*—*l Anemone.*

*Diameter across face.*—Approximately 35 mm. on average.

*Diameter across disc.*—Varies considerably and commonly can range from approximately 8 to 35 mm. under greenhouse growing conditions.

B. *Corolla of ray and disc florets.*—*Color (General tonality from a distance of three meters).*—Reddish with the adaxial coloration commonly being lighter. *Color Disc florets.*—When immature Greyed-Purple group 183A to 183B, and approaches Greyed-Red Group 179A on the upper surface and 179B on the under surface when fully mature. The coloration lightens as flowers mature (as illustrated). The disc florets are darker than the ray florets (as illustrated). Color ray florets. When immature Greyed-Red Group 179A on the upper surface and Greyed-Red Group 176D on the under surface. The coloration lightens as the flowers mature (as illustrated). For instance the ray floret coloration on the upper surface approaches Greyed-Red Group 179D when fully mature.

C. *Reproductive organs.*—Androecium—Not present. Gynoecium.—Present in disc florets and in ray florets.

Plant:

*General appearance.*—Height.— Medium tall. A height of approximately 30 to 40 cm. commonly is achieved throughout the year while utilizing an Alar growth retardant.

B. Foliage.—Color (abaxial).—Green Group 138A. Color (adaxial.—Green Group 137A to 137B. Shape.— Cordate.

I claim:

1. A new and distinct cultivar of Chrysanthemum plant named Red Champion substantially as herein shown and described, which:

(a) exhibits attractive flat bi-toned reddish anemone flowers wherein the disc florets are darker than the ray florets,
(b) exhibits a flower response period of approximately seven to eight weeks,
(c) forms flowers that exhibit a good vase life,
(d) exhibits a reduced susceptibility to leafminers, and
(e) has the ability to produce flowers of commercially acceptable quality throughout the year.

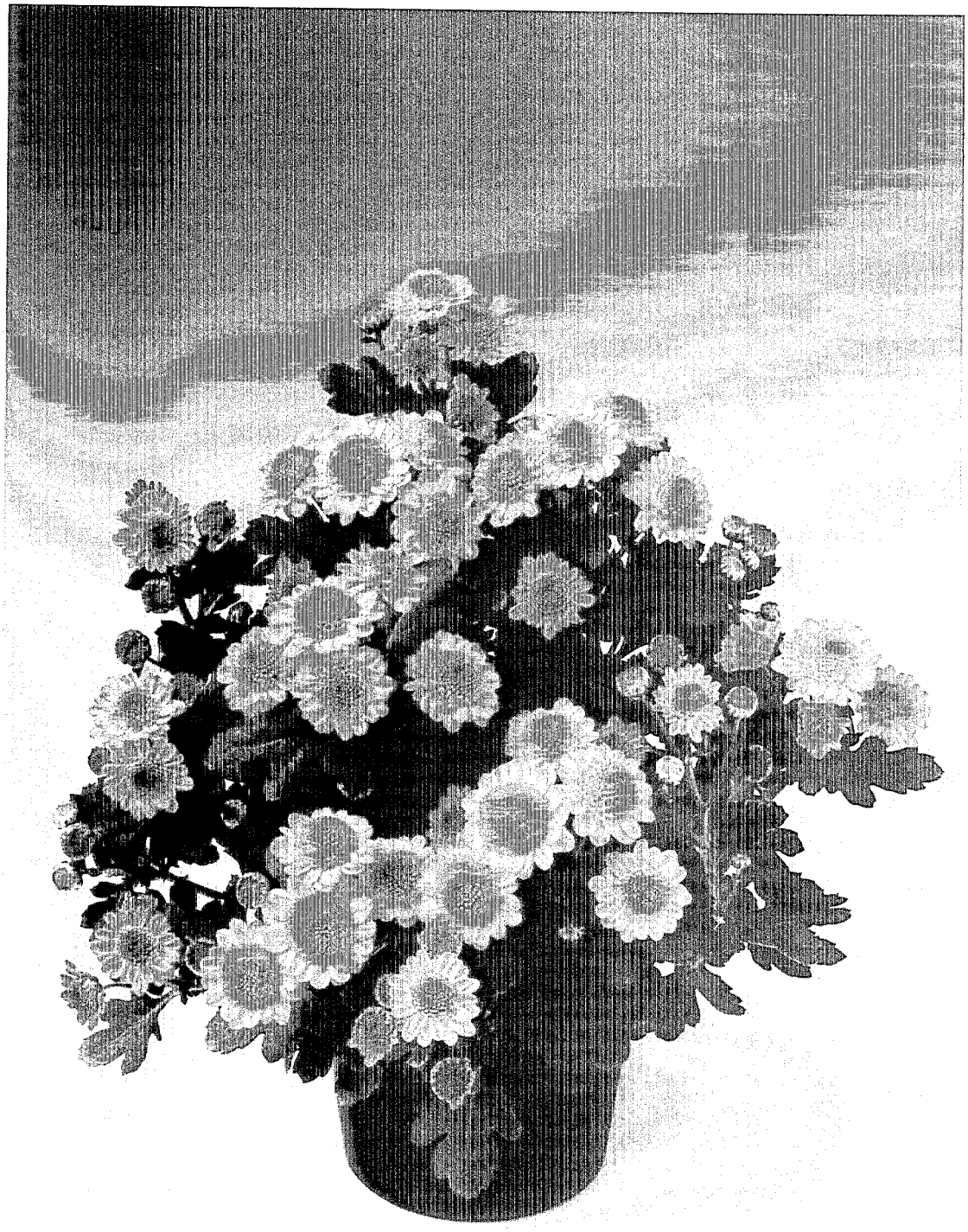

* * * * *